United States Patent [19]
Tucker

[11] Patent Number: 5,291,888
[45] Date of Patent: Mar. 8, 1994

[54] HEAD SENSOR POSITIONING NETWORK

[75] Inventor: Don M. Tucker, Eugene, Oreg.

[73] Assignee: Electrical Geodesics, Inc., Eugene, Oreg.

[21] Appl. No.: 750,107

[22] Filed: Aug. 26, 1991

[51] Int. Cl.⁵ .......................................... A61B 5/0478
[52] U.S. Cl. ................................................... 128/644
[58] Field of Search ............... 128/644, 639, 802, 803, 128/791; 607/149, 153

[56] References Cited

U.S. PATENT DOCUMENTS

| | | |
|---|---|---|
| 3,490,439 | 1/1970 | Rolston . |
| 3,508,541 | 4/1970 | Westbrook et al. . |
| 3,735,753 | 5/1973 | Pisarski . |
| 3,998,213 | 12/1976 | Price . |
| 4,033,334 | 7/1977 | Fletcher et al. . |
| 4,085,739 | 4/1978 | Sams . |
| 4,308,873 | 1/1982 | Maynard . |
| 4,323,076 | 4/1982 | Sams . |
| 4,537,198 | 8/1985 | Corbett . |
| 4,709,702 | 12/1987 | Sherwin . |

OTHER PUBLICATIONS

Hanley et al, "Electrode Systems . . . Subjects", Biomedical Electrode Technology, Academic Press, pp. 283-313, 1974.

Primary Examiner—Lee S. Cohen

[57] ABSTRACT

A method for positioning measurement sensors on the human head in which the surface of the head is partitioned into geodesic triangles by elastic lines connecting the sensors in a mutually-balanced tension network. The number of regularly-spaced sensor positions is selected by varying the number of geodesic partitions of the basic triangles of the icosohedron (10) or dodecohedron that form the initial solid polygonal partitioning of a sphere. The hemispherical structure of the network may be anchored at the perimeter by a headband (11). As the network is applied to a person's head, its balanced tension lines systematically conform its geodesic structure and thus the sensor positions, to achieve an even surface distribution of the sensors for that person's unique head geometry.

2 Claims, 2 Drawing Sheets

HEAD SENSOR POSITIONING NETWORK

FIELD OF THE INVENTION

This invention is within the field of medical and scientific instruments, in which sensors for measuring the brain's anatomy or function are applied to the head. The specific application of the preferred embodiment is electroencephalographic (EEG) recording of the brain's electrical fields, in which the sensors are electrodes contacting the scalp surface.

CROSS-REFERENCE TO RELATED APPLICATIONS

This application is related to my U.S. Pat. application submitted concurrently entitled "Head Sensor Positioning Pedestal." The head sensor positioning pedestal rests on the scalp directly, allowing the positioning network of the present application to be suspended above the hair, thus achieving a comfortable and secure attachment of an array of sensors to the human head.

DESCRIPTION OF PRIOR ART

A number of inventions (U.S. Pat. No. 3,735,753 to Pisarski, 1973; U.S. Pat. No. 4,033,334 to fletcher et al, 1977; U.S. Pat. No. 4,323,076 to Sams, 1982; or U.S. Pat. No. 4,308,873 to Maynard, 1982) have presented new holding devices for applying EEG scalp electrodes more quickly than is possible with the conventional method, in which each electrode must be glued to the scalp. The design of the individual scalp EEG electrode itself has been improved repeatedly (such as in U.S. Pat. No. 3,508,541 to Westbrook et al, 1970), and it is not the subject of my invention. At this time, sensors for other modes of neuroimaging, such as scintillation counters or radiological measures or superconducting quantum interference device magnetometers for magnetoencephalography (MEG), are large and heavy enough that they must have external supports. But with advances in sensor technology and miniaturization, the art of EEG electrode application and positioning may be applied to efficient implementation of other neuroimaging sensors as well.

In several examples of the prior art, holding devices comprising elastic straps or fabric have been used to adjust the positioning of electrodes to the various shapes taken by human heads (U.S. Pat. No. 3,490,439 to Rolston, 1970; U.S. Pat No. 4,709,702 to Sherwin, 1987; U.S. Pat. No. 4,537,198 to Corbett; 1985). These methods have had limited success in meeting two fundamental objects of electrode apparatus: (1) positioning the electrodes at the desired location in a way that adapts systematically to individual head geometries, and (2) attaching the apparatus to the subject's head comfortably and securely.

In one invention, Price (U.S. Pat. No. 3,98,213, 1976) recognized that elastic straps could be used to position scalp electrodes at proportional distances between skull landmarks as specified in the International Ten-Twenty System. In the Ten-Twenty System, a line from the nation (between the eyes) to the inion (skull at top of neck) bisects the head between left and right, and a second line from the left external auditory meatus (ear canal) to the right one bisects the head between front and back. Each of these lines is partitioned at intervals of 10% or 20% of its distance, and further lines connecting these intervals and intersections are used to specify the locations of 19 electrodes. These locations are recognized by the medical community as conventional recording sites. The electrodes of Price's invention are attached to elastic straps at 10%, 20% etc. of their length, thus aligning the electrodes at the target sites as the straps are stretched to fit the subject's head.

Because the elastic straps are placed directly on the meridian lines that are to be partitioned in the 10-20 System, Price's method has an important advantage over elastic caps in positioning 10-20 System electrodes accurately for different head shapes (whose primary lines of structural tension, as explained below, are haphazard). However, in Price's method, the elastic lines that are suited to dividing the measurement meridians are poorly suited to holding the apparatus on the head. The tension is limited to the top half of the head surface, and experience shows this causes an elastic strap apparatus to tend to pop off the top of the head. Applying an opposing tension, such as through a chest or chin strap, distorts the elastic likens at the point(s) at which this tension is applied.

One solution is to increase the tension of the existing straps, so they hold on to the head more securely. This is problematic with head straps because the straps typically rest on hair, which slides easily. The tension inequities work gradually, but inexorably, against the holding friction. The result is that tighter straps eventually pop the apparatus off the top of the head more energetically.

The only solution is to use enough tension around the main axial headband to balance the combined tension of the tops traps. This produces inequality of tension on the electrodes, which detracts from the object of equal electrode impedances.

A more serious problem with elastic straps is caused by the way they apply pressure along a long line of skin. This pressure serves to cut off the flow of blood through the vessels of the skin that pass under that line. Thus even with moderate pressure straps can restrict blood flow to large expanses of skin, and an apparatus that may seem comfortable for the first minute of wearing may be come an effective torque device after 20 minutes.

Those EEG electrode inventions using elastic material in caps, such as the inventions by Corbett or Sherwin cited above, also suffer from the problem of poor friction against the head because they are mostly gripping against the hair. In theory, elastic fabric could be an excellent device for adapting to various head geometries, given that it can distribute tension evenly across a surface. However, none of the cap designs in the prior art have been designed with a geometry to provide an even distribution of the elastic tension, mainly because of the hair problem. Because they cannot gain a workable purchase by applying pressure against the hair, the cap designs in the prior art must be held on the head by a strap or straps affixed to the chin, arms, or chest (see also U.S. Pat. No. 4,085,739 to Sams, 1978). The lines of structural tension, i.e., the vectors along which the elastic tension is focused, radiate from the point where the chin or body straps are attached to the cap toward the top of the head.

When the elastic cap adapts to differing head geometries, its adaptation, the degree of stretch, is also focused along these primary tension lines. The stretch is determined not only the by deviation of the subject's head geometry from the relaxed shape of the cap, but by the tension placed on the chin or body straps. The forced holding the electrodes against the head differs as well depending on the proximity of each electrode to the tension lines. The stretch of the cap is typically greatest along the sides, whereas the pressure against the head is typically minimal on the sides and greatest against the top of the head.

Thus because they occur by default rather than by design, the primary lines of structural tension in previous cap designs are haphazard, causing the confirmation of the cap to head geometries, and thus the proportional location of the electrodes, to be both uneven and poorly characterized.

Increasing the spatial density of scalp electrode arrays has recently become an important goal in the neuroimaging field. Sensitive electronic amplifier can now be constructed in multichannel arrays quite inexpensively. Researchers are producing new methods for mathematical analysis and graphic visualization of the brain's electrical fields. These methods can be implemented, on increasingly inexpensive computer workstations, to produce images of the brain's electrical fields within an anatomical reference frame, such as provided by a magnetic resonance image (MRI) of the brain and skull. The limiting factor in realizing the promise of these advances is the lack of a comfortable and efficient dense electrode array.

To my knowledge, no previous invention has attempted to achieve the primary object of my invention, which is an even spatial distribution of a dense array of sensors (e.g., 32, 64, 128, or more) across the surface of the head. The efforts in the previous art have assumed the traditional practice of placing electrodes either without reference to an explicit head-geometric pattern or at the 10–20 System locations. I have detailed the defects of the inventions in the prior art of EEG electrode application to show that these inventions could not be generalized to achieve a spatially regular, systematically comfortable, surface distribution of sensors on the head.

OBJECTS AND ADVANTAGES

The major object of this invention is to position a dense array (e.g., 32 or more) of EEG electrodes or other small, lightweight sensors, such that they are distributed evenly over the surface of the head to provide an optimal spatial sampling of the brain's anatomy and/or function.

Because this object of an even spatial distribution of the sensors must be implemented with they varying head geometries of individual subjects, the head sensor positioning apparatus should provide a systematic, deliberately constrained method for conforming its surface, and thus the spatial dispersion of the sensor, to the variety of shapes taken by actual human heads. Optimally, this confirmation method would allow a direct translation of the actual sensor locations on an individual's head to the corresponding locations on the simplest mathematical model of head geometry, the sphere.

Another object is to provide a secure and comfortable attachment of the apparatus to the head. Therefore the primary friction contacts with the head should be with the scalp directly, with no hair interposed between the friction contact points and the scalp. To distribute the weight and tension of the network across the head comfortably, there should be many of these scalp contact point, thus providing both comfort and adequate friction with the scalp, and, optimally, the scalp contact points would be the sensors themselves. Comfort would be further enhanced if the tension of the network were insured to be evenly distributed across these contact points.

These objects are important to the positioning of any spatially distributed array of head sensors. In the case of EEG electrodes, achieving these objects would allow the placement of sponge electrodes under the hair in contact with the scalp directly in a uniform and stable configuration, thus attaining the goal of an easily applied dense scalp electrode array.

To achieve these objectives, I have invented a head sensor positioning network, with the preferred embodiment at this time being a dense scalp array of EEG electrodes. Sponge electrodes, held within tubular sensor pedestals, are held upright on the scalp by an interlocking network of elastic threads. The structure of this network is comprised of geodesics, triangles that evenly partition the surface of a sphere. The present application is for patent protection for the method of regular spatial positioning of the sensors with the tension structure. As described above, the invention of the sensor pedestal is the subject of a separate patent application.

The crux of this design is achieving the even surface distribution of sensors by partitioning the geometry of a sphere into regular parts. A human head is not spherical, but it is spheroidal, and the sphere is the best simple mathematical approximation to its shape. Drawing on spherical geometry offers important structural advantages, achieving not only optimal regularity in the spatial dispersion of sensors across the surface of the head, but optimal mechanical integrity of the sensor positioning network from a minimum of elastic tension.

Drawing on spherical geometry also offers important data analytical advantages. Because the sensors are held in a geodesic pattern that conforms to the head's spheroidal surface, the actual 3-dimensional physical locations of the sensors can be translated systematical to homologous positions on the surface of a sphere. A mathematical model in which the head's geometry is simplified to a spherical shape is required to allow computationally tractable analysis of the localization of electromagnetic fields in the 3-dimensional matrix of brain and head tissue. Although today's common medical use of the EEG does not yet involve mathematical models of electrical fields in head tissue, the cutting edge of scientific research on the EEG and MEG does depend on these models, and the clinical applications will likely follow soon.

In one approach, researchers analyze the distribution of electrical fields across the scalp surface. Even with a dense electrode array, going from discrete EEG voltage recordings to characterize a voltage surface requires an interpolation algorithm. The most elegant and accurate interpolation algorithm known at this time is based on spherical spines. These are mathematical functions describing the surface of a sphere. When perturbed by (i.e., anchored to) voltage amplitudes at the appropriate locations, these spleens yield solutions for the voltage amplitudes as they would appear across the entire sphere surface. Even with powerful computers, solving the mathematics for these splines is practical only when the model is simplified to a spherical, rather than actual head-shaped, geometry.

In another research, hypotheses about the location of dipole electrical sources in brain tissue are evaluated by computing the scalp electrical fields that would be observed if these sources existed, then comparing these projections with the observed fields. In these computations, the model of 3-D geometry for volume conduction of the electrical fields includes conductance components for brain, skull and scalp. To be computationally tractable with today's computers, each of these conductance shells must be assumed to be spherical.

Because of its geometry, the geodesic head sensor apparatus I have invented conforms itself to a subject's head geometry in an optimal systematic fashion, by positioning the sensors on whose locations that would define the geodesic partitioning of the subject s head surface if that head were spherical in shape.

This positioning optimizes electromagnetic or other computations in which the head geometry is simplified to a spherical model. The actual 3-D locations on an indiviudal's head must be measured (as with a 3-D digitizer). But the partials coordinates of each sensor for the spherical generalization of the head are given simply by its position in the the geodesic network. Thus the distortion of spherical geometry required to describe that subject's head is characterized efficiently as the difference between the real vs idealized spherical coordinates. Once computations are performed within a spherical mathematical model, the head sensor positioning apparatus has provided the optimal positioning of the sensors for back-translating the results to the subject's actual head geometry. There the data can be localized within the anatomical framework of that subject's head space, such as with reference to anatomical images from volumetric MRI. for both research and clinical purposes, an accurate characterization of head geometry is becoming a critical requirement for all methods of neuroimaging.

Positioning the sensors in an exact spherical confirmation is only one of the options afforded by the geodesic structure of the network. If regularity of spatial dispersion dross the surface of the individual's actual head geometry is desired, the geodesic tension lines can be adjusted to approximate this goal or a range of head shapes, or, with more painstaking adjustments, for one person's head geometry fairly exactly. Even if framing the sensor positions spherically for mathematical modelling is not required the geodesic structure of my invention provides an optimal solution to the problem of systematically conforming the tensional structure of the positioning apparatus, and thus the surface distribution of the sensors, to fit individual head geometries.

The prior art for partitioning the surface of a sphere was advanced 24 centuries ago by the work of Platok who found that approximations to a spherical surface were approached most closely by the solid polygonal structures of the dodecohedron and icosohedron. More recently, Buckminster Fuller found that by further partitioning the triangular subunits of these polygons into smaller triangles, and allowing the angle sat the vertices of the major polygons to relax somewhat, a close approximation to a spherical surface could be achieved by an organization comprised solely of straight lines. The straight lines are structurally significant because they provide the simplest vectors for the forces of either tension or compression. Fuller described the partitioning triangles as"geodesics." this term became widely used for the hemispherical dome structures comprised of this geometry.

In its applications in architecture, the geodesic design optimizes the strength of a building and minimizes the stress on its structural members. In his search for elegant structural efficiency, Fuller emphasized that all material stress reduces to the forces of tension and compression. The geodesic dome optimally distributes the forces of compression caused by the action of cavity on the architectural structure. In my invention, the geodesic structure distributes the tension of the structural network evenly across the locations of the individual sensors.

Elastic threads are used to form the tensional structure in this embodiment. They create a network of triangles. The sensor is placed at the vertex of 6 triangles except at the vertices of the icosohedron where 5 triangles meet). The combined, uniform tension of the 5 or 6 lines that is into balanced within the elastic network itself is translated to a vector directed from each polygonal vertex radially toward the center of the sphere. This results in a compression of the sensor against the scalp along that radial vector.

The network thus realizes two forces from the elastic tension. One is balanced within the tension network itself, within the plane of the approximately spherical geodesic surface. The other is the radial force exerted through the sensor against the head. Because the sensor positioning network does not encircle the entire head, an anchoring force must be used at the perimeter; this is accomplished by an elastic headband of somewhat greater tension than the elastic net lines. But even here much of the tension exerted by the headband is balanced by that of the network itself, and the remainder is applied in a mostly radial direction through the perimeter sensors attached to the headband, rather than through the strap against the skin.

The design thus achieves the most important objects for a head sensor positioning apparatus. It limits the application of tension almost exclusively to the sensor-scalp contact points, achieving both an effective friction purchase and an economy of design. It optimizes the uniform distribution of tension across the multiple sensor sites, creating specific advantages such as uniform impedances for specific sensors such as EEG electrodes, and affording the general advantage of subject comfort y insuring adequate blood flow across all scalp regions.

Figure 1:
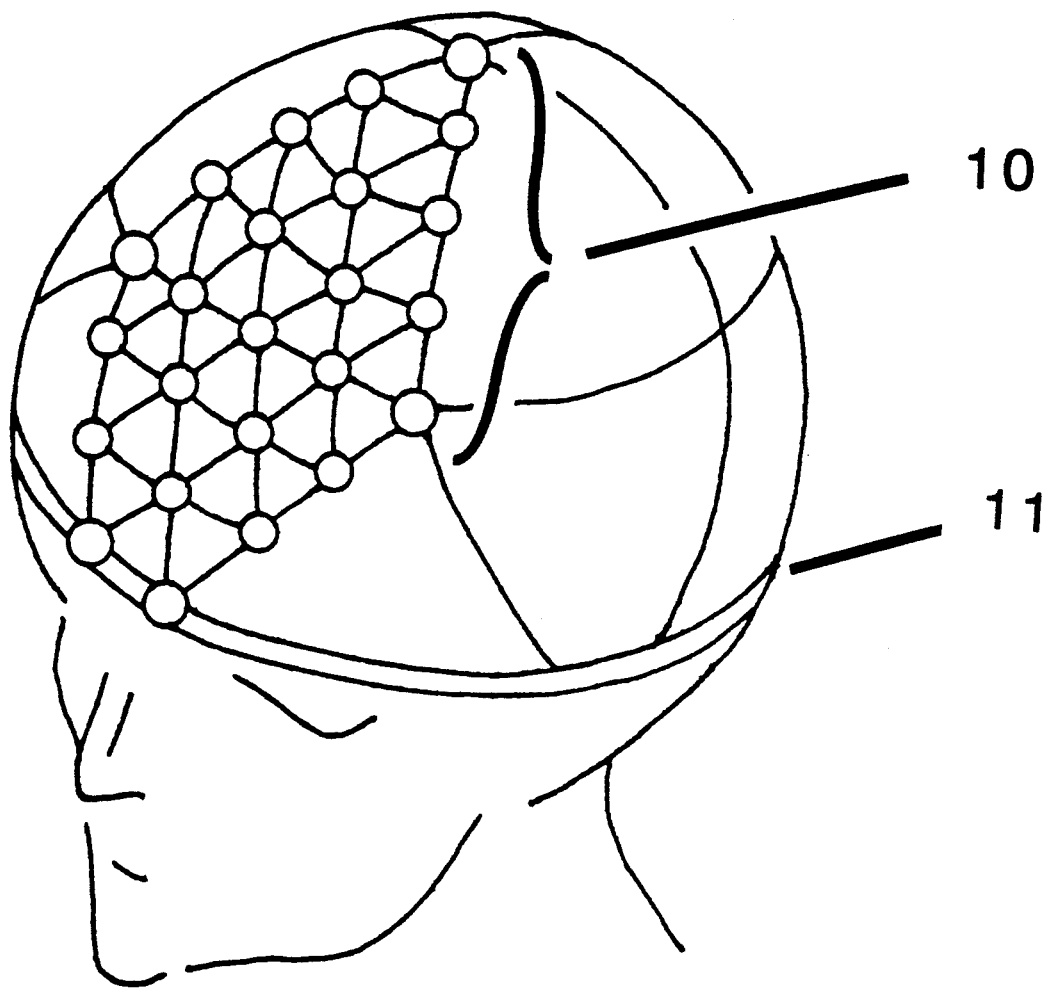
FIG. 1 is a view of the head sensor positioning network s it would be applied to a subject's head, showing the sensor pedestals that comprise two triangles of the icosohedron.

LIST OF REFERENCE NUMERALS 10 basic triangle of the icosohedron
11 perimeter headband

SPECIFIC DESCRIPTION OF FIGS. 1 AND 2

FIG. 1 illustrates how the individual sensor pedestals are linked by the elastic thread to form the geodesic structure of the head sensor positioning network. Pedestals forming 2 triangles are shown, but in a working sensor positioning network all vertices of the geodesic structure above the headband (11) are populated with electrodes. The icosohedron underlying this partitioning of the sphere comprises 20 triangles, which I call "basic" triangles to distinguish them from the smaller geodesic triangles. The vertices of the basic triangles are marked by pedestal collars having a pentagonal rather than hexagonal shape, since 5 rather than 6 tension lines form the vertices of the icosohedron. In the preferred embodiment, these pentagonal collars are made of colored plastic to allow the technician applying the net to maintain a clear visualization of the geodesic structure.

Figure 2:
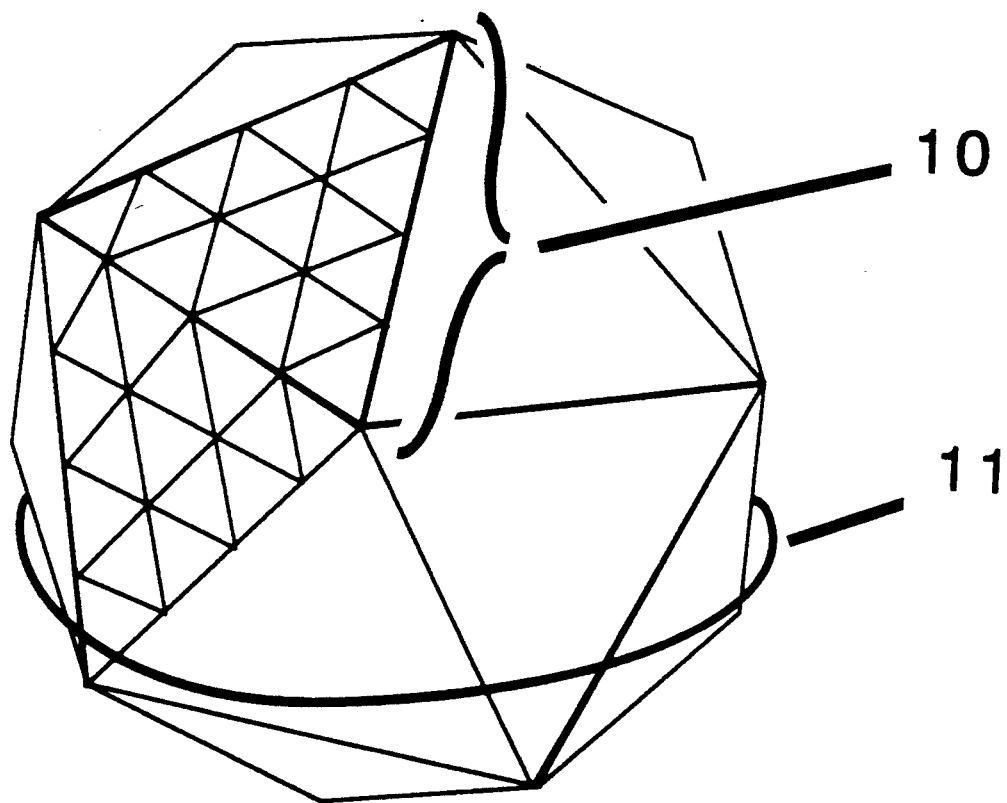
FIG. 2 shows the geometry underlying the partitioning of the sphere into the triangles of the icosohedron, and the partitioning of those triangles to achieve the vertex density (111) of this embodiment (suitable for a sense EEG array of 128 channels).

In FIG. 2, the icosohedron is shown with its vertices unrelaxes, thus demonstrating how the icosohedron geometry underlies the geodesic structure of this embodiment. When all the vertices distribute the structural tension or compression evenly, the result is a more spherical, geodesic structure, From FIG. 2, it can be seen that, from the orientation of this viewing angle, 5 of the basic triangles could be described as a pentagonal pyramid at the top of the icosohedron, Ten basic triangles would be said to form the middle section of the icosohedron, with 5 remaining triangles forming the pentagonal pyramid on the underside.

For this 128-channel embodiment of the sensor net, the geodesic partitioning of the basic triangles has been designed to create 111 vertices (and thus electrodes) within the hemispherical structure above the headband (11). A pattern that is repeated 5 times is comprised of the unique vertices of one basic triangle of the top pyramid (10) plus those of two partial basic triangles of the middle section. Omitting the bottom row of these partial triangles (which is below the headband), and omitting the topmost vertex of the top pyramid (which is shared by all 5 triangles of the top pyramid), there are 22 vertices, and thus 22 electrodes, in the repeating pattern, and therefore 110 when the pattern has repeated 5 times around the head. Together with the shared topmost vertex (shown in FIG. 1 with a pentagonal collar), this makes 111 electrodes for the scalp surface. This embodiment allows the remaining channels of a 128 channel amplifier system to be devoted to adhesive skin electrodes or nasopharyngeal electrodes external to the sensor positioning network. These external electrodes are important for sampling the electrical fields below the headband, thereby sampling the volume conduction of rain electrical fields throughout the head space.

In this embodiment, the perimeter headband (11) is placed such that the bottom row of electrodes sits on the supra orbital ridge (eyebrows) then rings the canthomeatal line (from the side of the eye socket of the hear canal and around the back of the head in a continuation of this line).

Not shown in FIG. 1 are the fine wires emanating from each electrode. In this embodiment they are gathered in a cable supported above the head and lugged into the bank of amplifiers mounted over the subject's head. With this arrangement, the subject has a comfortable range of movement during the recording session, but when sitting still for critical recording periods the weight of the wires is completely supported and does not impinge on the lightweight sensor positioning network.

The deviation of the typical human head from a spherical shape can be considered at the time the tension of the geodesic elastic lines is adjusted. The construction template is a model of an average-shaped human head of the desired size, marked with the target positions of the sensor pedestal feet as they are formed by conforming the spherical geodesic structure to the spheroidal head shape. This initial modal confirmation decreases the tension stress produced by the further conformations required for fitting actual heads.

In the preferred embodiment, the sensor pedestals at the vertices of the geodesic triangles are populated with simple Ag/AgCl electrolyte sponge electrodes, as described in the concurrent patent application for the sensor pedestal. Other EG electrode embodiments, such as that of Westbrook et al (U.S. Pat. No. 3,508,541, 1970) could easily be implemented within this design. Although more costly, the Westbrook et al design may offer the advantage of being relatively insensitive to movement artifact.

It should be apparent that the particular choices of the geodesic structure made of the preferred embodiment are only some of many options possible for the embodiment of this invention. I have implemented this invention with sensor nets for 32- and 64-channel EEG systems as well. Predictably, the stability of the design improves with a greater number of pedestals. Buckminster Fuller spelled out simple methods for achieving the desired number of vertices in a geodesic structure. As shown in its architectural applications, the geodesic design offer snot only optimal structural efficiency but great flexibility in meeting the requirements of specific instantiating.

OPERATION OF THE INVENTION

The application of the sensor positioning network (net) begins s the technician dips it in a container of saline electrolyte to wet the sponges, then shakes the excess saline from it gently. The technician then holds the net in a dome shape by supporting it on the backs of the spread fingers of both hands. Facing the subject, and visualizing the geodesic structure of the basic triangles to orient key pedestals with skull landmarks, the technician holds the peak icosohedron vertex against the vertex of the skull (where the nasion-inion line crosses the line connecting the ear canals) and moves the net in slight back-and-forth motions to seat the pedestals on the crown of the head, allowing them to part the hair they encounter. The process continues by spreading the net known of the head, relying now on the tension against the crown, while moving the net slightly to seat each sensor pedestal. The positioning should allow each pedestal to come to rest on the head very hear its target location, such that when the headband is placed on the canthomeatal line, very little adjustment of the overall net position is necessary (and thus very little of each sponge's saline load is lost among the hair). Next, each sensor pedestal is inspected for radial alignment, and for the adequate contact of its foot directly against the scalp during this inspection, the seated pedestal feet are allowing the electrolyte to hydrate the scalp, improving the impedances. Then, relying on a computer display map or other monitor of the electrode impedances, the technician finds any electrode sensors with impedances higher than the criterion, and seats each one against the scalp by grasping the collar and scrubbing the foot gently against the scalp. This completes the lifting of the hair away from the foot (see the concurrent patent application for the sensor pedestals) and achieves adequate scalp contact.

With these procedures, successful application of the sensor positioning network with EEG electrodes has been achieved within half an hour for most subjects. With further refinements, a 15-minute application time is not unreasonable. For the first few minutes after application, the excess saline may wet the scalp and hair between the electrode pedestals. These areas soon dry out, however, so that the only wet areas are the areas of scalp beneath the sponges. With minimal individual attention, the impedances of the electrodes typically range from 10K to 50K ohms.

This range of impedances, including both the general level and the variation among electrodes, is higher than would be acceptable in traditional EEG recording practice. However, modern electronic amplifiers such as those relying on low-noise field-effect transistors can provide input impedances in excess of 100 meg ohms, significantly beyond the range of electrode source impedances provided by the EEG electrode sensor net. I have made many recordings with 64-channel nets using amplifiers having input impedances in this range. These nets yielded consistently clean, artifact-free EEG signals. The only disadvantage of the sensor positioning network over conventional (non-sponge, 3K ohm impedance) electrodes is a somewhat greater sensitivity to movement artifacts.

An important advantage of the design is the even distribution of tension across the electrode feet. Although the preferred embodiment with elastic thread allows substantial stretch to fit individual heads, optimal EEGs and excellent subject comfort are achieved when the net is stretched a consistent, moderate amount. Therefore in the preferred embodiment, three sizes of net have been constructed to achieve optimal tension for adjust human head sizes. With these optimal tension levels, subjects can wear the not for several hours with minimal discomfort. This is not the case with conventional cap designs, particularly when the cap tension must be maintained with elastic chin or chest straps.

With normal usage, and occasional sponge replacement, the net holds up to many recording sessions. Complete viral and bacterial sterility is insured by soaking the net in a commercial hospital disinfectant after each use.

For EEG analyses that are to be referenced to anatomical locations such as with an MRI, digitization of each electrode position in 3D may be required. However, because of the strong regularity of positioning achieved by the geodesic net, it may be feasible to digitize the actual location of electrodes in key positions, then algorithmically determine the positions of the remaining electrodes on the anatomical image of the subject's head surface, since these intermediate positions are tightly constrained by the net tensions.

Although the preferred embodiment of the head sensor positioning network at this time is a dense EEG electrode array, it is quite likely that technological advances will require the positioning of dense sensor arrays for other recording purposes. For example, as high-temperature superconductors improved, new magnetometer designs may allow dense arrays of MEG sensors. These would need to be positioned with reference to individual head geometries.

SUMMARY, RAMIFICATIONS, AND SCOPE

Thus various measurements of brain activity and structure may present common requirements for sensor positioning that are solved by my invention. The novel features and advantages of the invention deal not with the specific embodiment of the dense EEG electrode array, but with the use of an explicitly organized tension network for systematic and efficient positioning of sensors on the head. The most important features and advantages may be summarized:

(1) A spheroidal tension structure is partitioned into regular polygons, with sensors located at regular points such as vertices of the polygons, such that the tension, distributed evenly across the surface of the structure, produces an even spatial distribution of the sensors across a subject's head surface. By explicit design and adjustment of the tension lines, an explicit confirmation of sensor positions to individual head geometries can be achieved.

(2) Because it is curved in a spheroidal shape, this structure translates part of its surface tension (tension in the curved plane of its surface) to radial compression (forces directed toward the approximate center of the spheroid head). Fixing the sensors at these specific points of radial compression allows them to be held against the head with the holding force applied in exactly the desired sphere-radial) direction. The strength of this holding force is easily adjusted to the desired level by adjusting the surface tension of the structural network. The regular geometry of the sensor positioning network assures that the radial compression forces will themselves be uniformly distributed across the array of sensors.

While my above description contains many specificities, these should not be construed as limitations on the scope of the invention, but rather as an exemplification of one preferred embodiment thereof. Many other variations are possible. For example, instead of a net comprised solely of elastic lines with sensor pedestals at the vertices, the effective arrangement of the geodesic structure might be achieved by other means. The sensor pedestals could be inserted in a loose nonelastic fish net, mesh, or cloth, and the geodesic arrangement could be formed into the desired structure by sewing the elastic geodesic lines in the spaces between the pedestals. The pedestals would then exist at the center of the geodesic triangles formed by the elastic thread, but an equivalent geodesic structure and an equivalent set of radial compression forces could be achieved.

For another example, the advantages of the invention may not be limited to an embodiment in which the tensional structure of the apparatus is solely responsible for holding the sensors against the head. An embodiment could be implemented in which the tensional structure of the head sensor positioning apparatus is used to achieve the critical object of systematically conforming the positions of heavier sensors, such as scintillation counters, to the subject's head geometry, even when the weight of the sensors must be supported by external means.

Accordingly, the scope of the invention should be determined not by the embodiments illustrated, but by the appended claims and their legal equivalents.

I claim:

1. An apparatus for positioning sensors on the surface of a human head comprising:
    (a) a plurality of sensors used for measuring brain anatomy or function,
    (b) a plurality of means for creating tension between pairs of said sensors,
    (c) means for arranging a tension network that systematically balances said plurality of means for creating tension based on partitioning the surface of a sphere into polygons, thereby causing said means of creating tension to adapt the positioning apparatus to the geometry of an individual head through a systematic conformation of the geometry of a sphere.

2. The invention of claim 1 further including the vertices of each polygon located equidistant from the vertex of each adjacent polygon whereby said equidistant position creates equal tension on each of said sensors resulting in equal radial compression being directed on each of said sensors.

* * * * *